(12) United States Patent
Groth et al.

(10) Patent No.: US 6,692,913 B1
(45) Date of Patent: Feb. 17, 2004

(54) PROCESS FOR DETERMINING CELL VITALITY

(75) Inventors: Detlev Groth, Perch (DE); Regina Reszka, Schwanebeck (DE)

(73) Assignee: Max-Delbruck-Centrum fur Mdekular Medizin, Berlin (DE)

( * ) Notice: Subject to any disclaimer, the term of this patent is extended or adjusted under 35 U.S.C. 154(b) by 0 days.

(21) Appl. No.: 09/571,338

(22) Filed: May 8, 2000

Related U.S. Application Data

(63) Continuation of application No. PCT/DE98/03245, filed on Nov. 6, 1998.

(30) Foreign Application Priority Data

Nov. 7, 1997 (DE) .......................................... 197 50 790
Feb. 13, 1998 (DE) .......................................... 198 05 818

(51) Int. Cl.[7] .............................. C12Q 1/68; C12Q 1/00; C12Q 1/42; G01N 33/53

(52) U.S. Cl. ................................ 435/6; 435/4; 435/7.1; 435/21

(58) Field of Search ................................ 435/4, 14, 21, 435/7.1, 6; 71/11

*Primary Examiner*—David Guzo
*Assistant Examiner*—Katherine F Davis
(74) *Attorney, Agent, or Firm*—Goodwin Procter LLP

(57) ABSTRACT

A process for determining cell vitality and efficiency after gene transfer in eukaryotic cells by measuring reporter gene activity, which comprises determining in a reaction vessel the cell count of the transfected cells by a representative enzyme activity, and ascertaining in the same reaction vessel the efficiency of the gene transfer by determining the reporter gene activity after changing the pH.

6 Claims, 5 Drawing Sheets

PROCESS FOR DETERMINING CELL VITALITY

This is a continuation of international application No. PCT/DE98/03245, filed on Nov. 6, 1997, and Feb. 13, 1998.

FIELD OF INVENTION

The invention relates to a method for the parallel determination of cell vitality and efficiency using a reporter gene after gene transfer in eukaryotic cells in the same culture vessel, as well as to a dual test system.

BACKGROUND

The application of DNA in eukaryotic cells is an important technique in molecular biology. For this purpose, a series of methods were described, such as the calcium phosphate precipitation method (Graham-F L; Eb-AJ-vander (1973), a new technique for the assay of infectivity of human adenovirus 5 DNA. Virology 52: 456–67), various virus-mediated methods (Rosen-C A; Sodroski-J G; Haseltine-W A (1985). The location of cis-acting regulatory sequences in the human T cell lymphotropic virus type III (HTVL-III/LAV) long terminal repeat, Cell 41: 813–23), the application of DNA with the help of cationic liposomes (Felgner-P L; Gadek-T R; Holm-M; Roman-R; Chan-H W; Wenz-M; Northrop-J P; Ringoldi-G M; Danielson-M (1987), Lipofection: a highly efficient, lipid-mediated DNA transfection procedure, Proc.-Natl-Acad-Sci-USA, 84: 7413–7) or of polymers (Fauci-A S (1986), Current issues in developing a strategy for dealing with the acquired immunodeficiency syndrome, Proc-Natl-Acad-Sci-USA, 83: 9278–83; Mosca-J D; Bednarik-D P; Raj-N B; Rosen-C A; Sodroski-J G; Haseltine-W A; Pitha-P M (1987), Herpes simplex virus type 1 can reactivate transcription of latent human immunodeficiency virus, Nature, 325: 67–70; Gendelman-HE; Phelps-W; Feigenbaum-L; Ostrove-J M; Adachi-A; Howley-P M; Khoury-G; Ginsberg-H S; Martin-M A (1986), Transactivation of the human immunodeficiency virus long terminal repeat sequence by DNA viruses, Proc.-Natl-Acad-Sci-USA, 83: 9759–63 and with the help of physical methods (O'Hare-P; Hayward-G S (1985), Evidence for a direct role for both the 175,000 and the 110,000 molecular weight immediate-early proteins of herpes simplex virus in the transactivation of delayed-early promoters, J-Virol. 53: 751–60, Gorman-C M; Moffat-L F; Howard-B H (1982), Recombinant genomes which express chloramphenicol acetyl transferase in mammalian cells, Mol-Cell-Biol. 2: 1044–51).

A series of so-called reporter genes is used, such as the LacZ gene (Lim-K); Chae-C B (1989), to investigate the efficiency of the gene application in the case of in vitro applications. A simple assay for DNA transfection by incubation of the cells in culture dishes with substrates for β-galactosidase is described in Biotechniques, 7: 576–9), the luciferase gene (Nordeen-S K (1988), Luciferase reporter gene vectors for analysis of promoters and enhancers, Biotechniques, 6: 454–8), the chloramphenicol acetyl transferase gene (Gorman et al. (1982), see above) and others. In comparison to other reporter genes, the LacZ gene offers various advantages. First of all, it is possible to stain individual cells, the transfected cells, expressing the reporter gene, with the help of so-called X-Gal staining (Lojda-Z; Slaby-J; Kraml-J; Kolinska-J (1973), Synthetic substrates in the histochemical demonstration of intestinal disaccharidases, Histochemie, 341–9). Furthermore, the total gene expression of a larger number of cells can be determined with the help of a simple color test (Lim and Chase 1989, see above). In contrast to a large number of other reporter genes, these determinations of the gene expression can be carried out in any laboratory, since only the measurement of the color developed is required, but no radioactive or luminometeric measurements.

Since most techniques, which apply DNA in eukaryotic cells, are accompanied by some cell damage, the determination of cell vitality after a gene transfer or the determination of the toxicity is of importance for characterizing the efficiency and safety of the method. A series of methods are available for determining the toxicity of compounds, which generally involve the measurement of the activity of a representative enzyme of the cells or the manual counting of the living cells. The enzymatic methods have gained the widest acceptance for investigating a large number of samples. In this connection, especially the so-called MTT test (Mossman-T (1983): Rapid colorimetric assay for cellular growth and survival: application to proliferation and cytotoxicity assays, J-Immunol-Methods, 65: 56–63) as well as the acid phosphatase test (Connolly-D T, Knight-M B, Harakas-N K, Witwer-A J, Feder-J (1986), Determination of the number of endothelial cells in culture using an acid phosphatase assay, Anal-Biochem. 152: 136–40), for which the activity of mitochondrial dehydrogenase (MTT) or of cytosolic acid phosphatases is determined are of particular importance here. Until now, there are only methods which determine, in separate batches either the efficiency of the method by way of the reporter gene activity or methods which determine the toxicity of the method by way of an enzyme activity which is representative of the number of cells.

DESCRIPTION OF THE INVENTION

The invention surprisingly enables a combination of a modified acid phosphatase assay with a colorimetric or fluorimetric reporter gene assay for the simultaneous determination of the cell vitality and of the expression of the reporter gene assay, suitably a β-galactosidase assay for the simultaneous determination of the cell vitality and of the expression of the reporter gene.

The present invention is a process for determining cell vitality and efficiency after gene transfer in eukaryotic cells, which comprises determining in a reaction vessel the cell count of the transfected cells by a representative enzyme activity, and ascertaining in the same reaction vessel the efficiency of the gene transfer by determining the reporter gene activity after changing the ionic strength and pH.

The present invention is also a dual test system for the above process, which comprises (a) a vitality assay with a substrate for determining acid phosphatase activity, and a buffer for cell lysis, and (b) a reporter gene assay with a substrate for the reporter assay, and a buffer for determining the efficiency.

BRIEF DESCRIPTION OF THE DRAWING

The inventions is explained below in greater detail with reference being had to the drawing, wherein.

DETAILED DESCRIPTIONS

Figure 1:
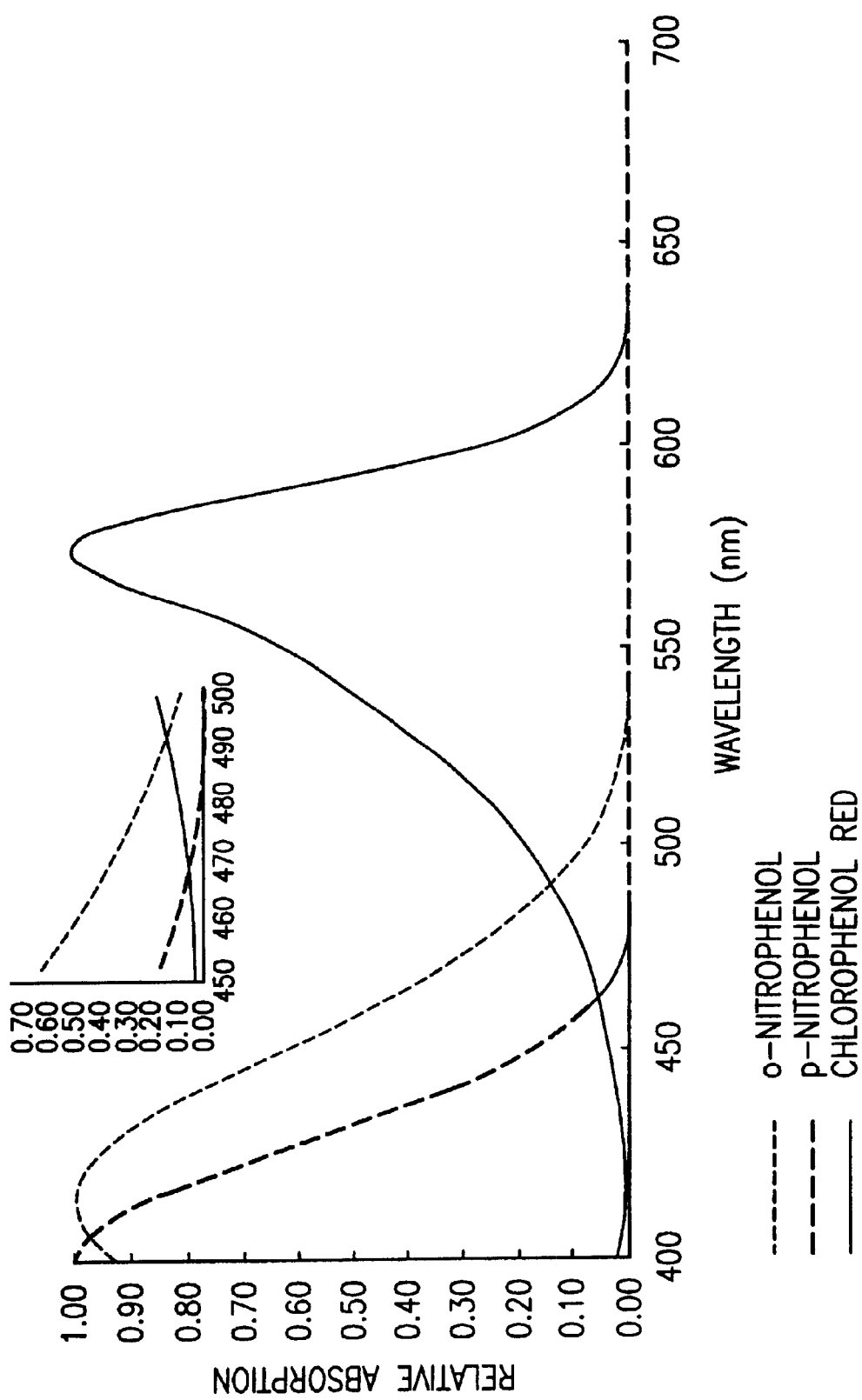
FIG. 1 is a comparison of the absorption spectra of reaction products of the enzyme substrates employed.

The cells, after expression of the reporter gene (24 to 72 hours after the transfection), are washed with phosphate-buffered salt solution (PBS). Subsequently, the buffer is added for the determination of the acid phosphatase, which suitably contains p-nitrophenyl phosphate (pNPP) as substrate, 2-morpholinoethanol sulfonic acid (MES) as buffer and alkylphenyl polyethylene glycol (Triton X-100) or naphthyl phosphate in sodium acetate/Triton X-100 for cell lysis. After a 15 to 30 minutes incubation at 37° C., the reaction is stopped by the addition of tris (hydroxymethyl) aminomethane HCl (pH 8.0) (tris HC1) or HEPES and the amount of reaction product (p-nitrophenol) is determined either spectrophotometrically at 405 nm or fluorimetrically. The level of the acid phosphatase activity determined is a measure of the number of living cells.

Subsequently, a β-galactosidase assay buffer is added to the same cell culture dish. This buffer contains CPRG or ONPG in Hank's Balanced Salt Solution (HBSS) and/or MUG in HBSS, extraction from the MUG stock solution into DMSO and HBSS. After an incubation period of 2 minutes to 24 hours, the amount of reaction products is determined spectrophotometrically at 540–580 nm or by fluorimetrics. Accordingly, the amount of chlorophenol red, for example, is a measure of the expression of the reporter gene.

A dual test system for the parallel determination of cell vitality and efficiency after gene transfer in eukaryotic cells comprises a) a vitality assay with (i) a substrate for determining the acid phosphatase enzyme, and (ii) a buffer for the cell lysis, as well as b) a reporter gene assay with (i) a substrate for this assay, and (ii) a buffer for determining the efficiency.

The test of the present invention for the first time permits determining the efficiency and toxicity of a gene transfer method in one preparation and also directly in the cell culture vessel. The method employed for this purpose uses the activity of the acid phosphatase enzyme as a marker for the vitality of the cells after the gene transfer and the activity of the gene product of the applied lacZ gene, the β-galactosidase activity, as a marker of the efficiency of the gene application. In the first step, the acid phosphatase activity is determined with the help of a modified assay. The pNPP substrate, preferentially offered to the acid phosphatase, is converted into p-nitrophenol and the amount of reaction product is determined photometrically by light absorption at 405 nm. The buffer, used for this determination, contains buffer substance in a concentration lower than that employed in previous methods and is suitable for the determination of the cell activity. Furthermore, after the determination of the acid phosphatase activity, the low ionic strength of the buffer used permits the pH to be changed from 5.5 to about 7.8 by the addition of an excess of tris HCl or HEPES buffer (pH of 8.0). After the addition of a β-galactosidase test buffer, this buffer mixture is suitable for determining the β-galactosidase activity in the preparation. CPRG, ONPG or MUG is used as substrate. The absorption maximum of the chlorophenol red reaction product of the β-galactosidase reaction when CPRG is used is at about 570 nm. With that, the spectrum of the p-nitrophenol reaction product of the acid phosphatase reaction, which is already in the preparation, does not interfere with the subsequent determination. In comparison to p-nitrophenol, the reaction product of the acid phosphatase reaction, the o-nitrophenol hydrolysis product, has an absorption spectrum, which is shifted to the longer wavelength region of light. This enables the β-galactosidase reaction to be determined, for example, at 490 nm. Methyl umbelliferone, as reaction product of the β-galactosidase reaction when MUG is used, can be determined fluorimetrically. The combination of two fluorescing substrates is also possible, if the emission spectra do not overlap. For example, naphthyl phosphate can be used as substrate of the acid phosphatase reaction and MUG as substrate of the β-galactosidase determination.

The inhibition of the β-galactosidase determination by the prior measurement of the activity of the acid phosphatase enzyme is less than a power of 10 and is acceptable, since the β-galactosidase enzyme is quite stable under the conditions used and the sensitivity of the test can be increased further by longer incubation times.

The method of the present invention can be used for characterizing gene transfer methods with respect to toxicity and efficiency. For the cell-count determination, the acid phosphatase test described is faster and more accurate than the widely used MTT test. Moreover, the use of toxic chemicals is reduced. In contrast to previously described methods, buffers of low ionic strength are used for the present method. This does not affect the sensitivity of the method, but permits the pH to be subsequently increased by the addition of a higher ionic, weakly alkaline buffer system. The conditions obtained thereby are advantageous for the subsequent determination of the second enzyme in the reaction preparation, namely the determination of the β-galactosidase enzyme. The activity of this enzyme is decreased only slightly by the prior determination of the acid phosphatase and is high enough for the determination of the reporter gene expression in all cell lines tested and in primary endothelium cells of bovine corneas. This test is very suitable for the comprehensive, rapid and inexpensive testing of the different methods or materials for a gene application.

The invention is explained in greater detail by the examples wherein the following abbreviations are employed.

MUG: methyl umbelliferyl-b-D-galactopyranoside
ONPG: O-nitrophenol-b-D-galactopyranoside
PBS: phosphate buffered saline
CPRG: chlorophenol red b-D-galactopyranoside
pNPP: p-nitrophenyl phosphate
pNP: p-nitrophenol
DMSO: dimethylsulfoxide
HBSS: Hank's balanced salt solution
Determination of the Absorption Spectra of p-Nitrophenol o-nitrophenol and Chlorophenol Red The pNPP substrate is converted in the cell culture into p-nitrophenol. For this purpose, the 10 mM pNPP substrate solution in 0.02 M MES (having a pH of 5.5) and 0.1% of Triton X-100 are added to an MCF-7 cell culture for the cell lysis. After incubating for one hour, the supernatant is taken off and the cell fragments are removed by centrifuging. After that, the spectrum is recorded using a spectrophotometer.

As shown in FIG. 1, the ONPG and CPRG substrates are hydrolyzed completely by the addition of a β-galactosidase standard in HBSS. Subsequently, the spectrum of the chlorophenol red and the o-nitrophenol reaction products are also determined in the visible light range.

β-Galactosidase Essay in Aqueous Media

Dilutions of a β-galactosidase standard in HBSS are prepared and 10 mL of this standard are added to single wells of a 96-well plate. The activity of the β-galactosidase enzyme, which is being tested, is between 100 and 0.0001 mU/well.

As buffers HBSS, HBSS with 0.1% Triton X-100 (HBSS-TX) as well as 0.02 M MES buffer, having a pH of 5.50 with 0.1% of Triton X-100 (MES-TX) are employed.

Figure 2:
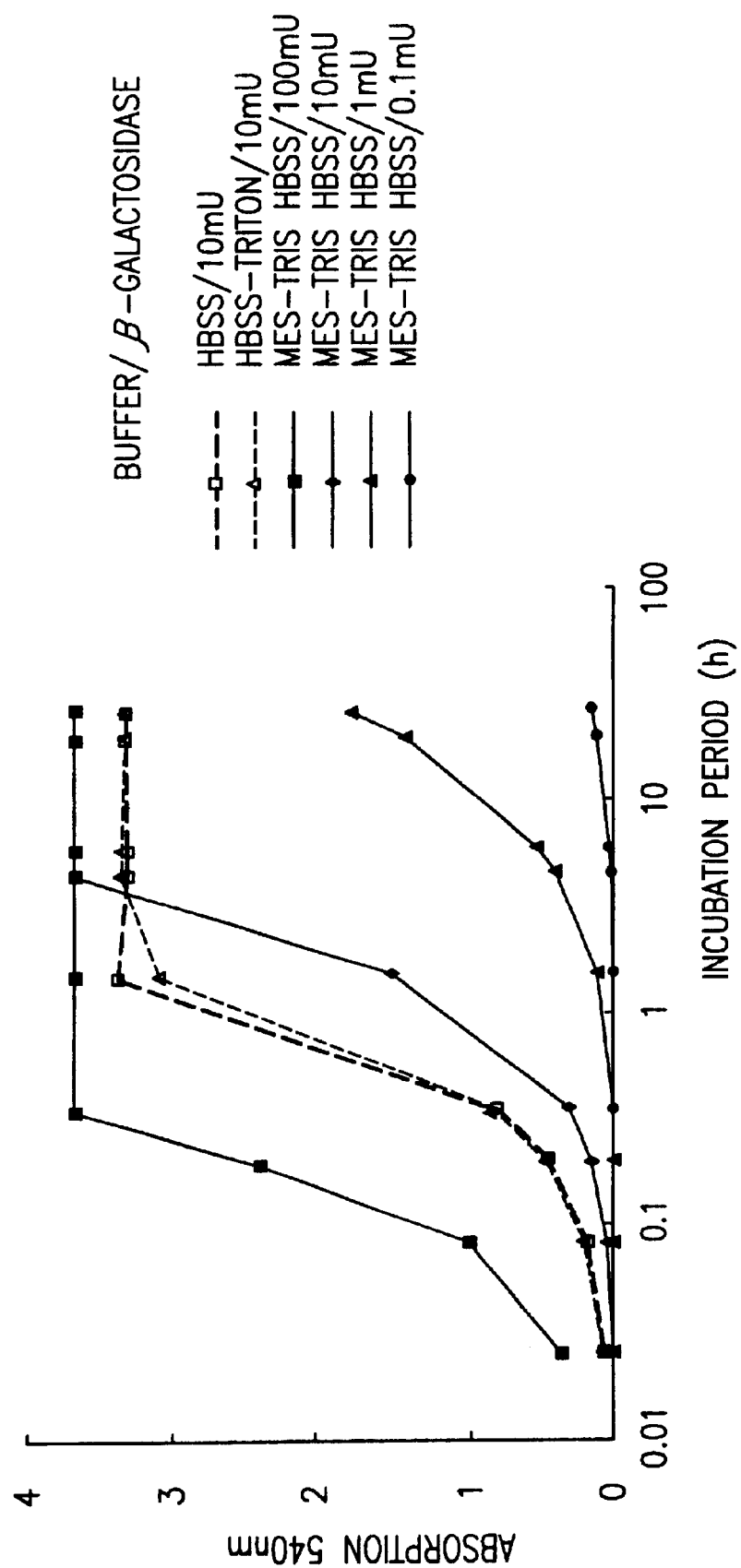
FIG. 2 is the β-galactosidqae reaction as a function of time in different buffers.

To each well with β-galactosidase standard, 100ml of HBSS or of HBSS-TX or 80 ml of MES-TX are added. Subsequently this was followed by an incubation for 30 minutes at 37° C. and 5% carbon dioxide. After that, 20 ml of 0.5 M of tris HCl or 20 ml of 0.5 M HEPES (with a pH of 8.0) are added to the wells with β-galactosidase standard and MES-TX buffer. This is followed by the addition of 150 ml of CPRG substrate solution with 1 mg/ml of CPRG, dissolved in HBSS. The optical density at 540–580 nm is determined a various times using a microtiter plate photometer as shown in FIG. 2. The activity of the β-galactosidase enzyme, which was tested, is between 100 and 0.01 mU/well. The following buffers were used: HBSS, HBSS with 0.1% Triton X-100 (HBSS Triton) as well as 0.02 M MES buffer, pH 5.5 with 0.1% Triton X-100 MES). To each well with β-galactosidase test standard, 100 ml of HBSS or HBSS and Triton or 80 ml of MES buffer are added. After incubation and buffering and adding of CPRG substrate solution, the optical density was determined.

Preparation of the Liposomes

Lipids are dissolved in trichloromethane and, after that, the trichloromethane is removed by evaporation and vacuum drying for several hours. The liposomes subsequently are prepared by the addition of deionized water and shaking vigorously for 2 minutes on a Vortexer.

Cell Culture

MCF-7, MaTu, CC531, 293 and LS174 cells are cultured in an RPMI 1640 medium and F98 cells, bovine cornea endothelial cells in Dulbecco's modified Eagle's medium (MEM) and N64, N39, U343 and U373 cells in a modified Eagle's medium (MEM). All media contain 10% fetal calf serum, 100 U/ml of penicillin G, 100 mg/ml of streptomycin sulfate and 0.25 mg/ml of amphotericin. The cells are cultured in the cell incubator with 5% carbon dioxide/95% air at 37° C.

Cell Count Determination

The cells are trypsinized and the cell count is determined with the help of the trypan blue staining and counting with the microscope. Subsequently, between 125 and 30,000 cells are sown per well of a 96-well microtiter plate. On the following day, the medium is removed and the adhering cells are washed once with phosphate buffered saline (PBS). For determining the cell count with the help of the MTT test, 100 ml of medium with 0.5 mg/ml of MTT reagent are added. After the cells are incubated for 3–4 hours at 37° C. and 5% carbon dioxide, the medium is removed and the formazan crystals are dissolved in dimethylsulfoxide. Subsequently, the optical density is determined using a microtiter plate photometer at 540 nm (with a 690 nm reference filter).

Figure 3A:
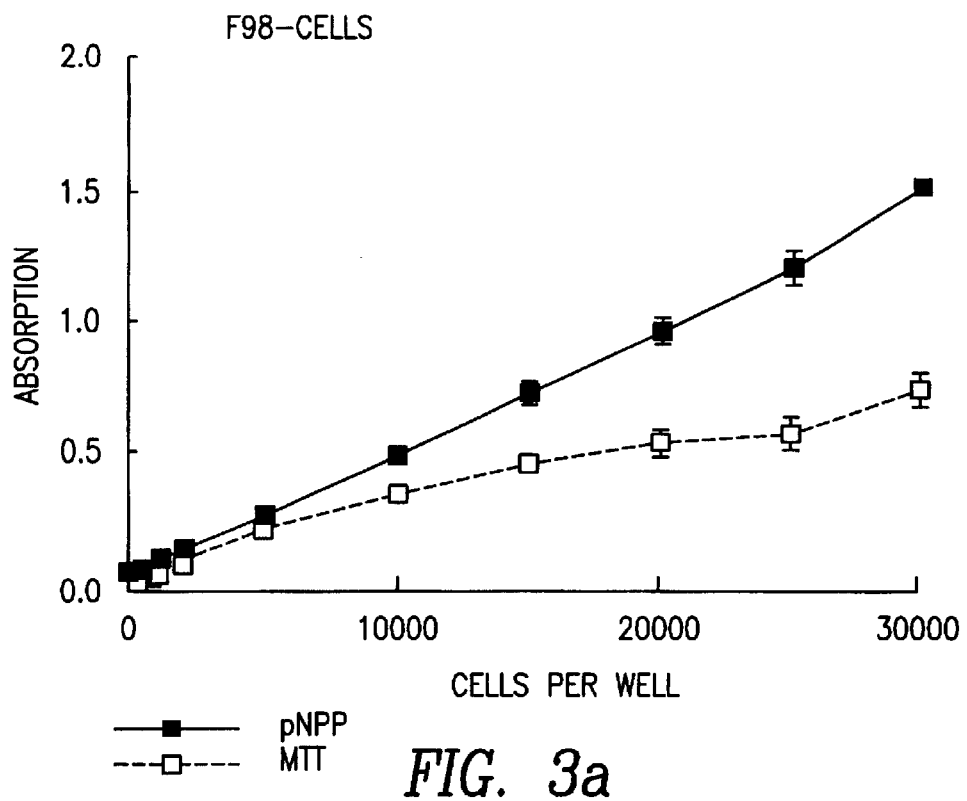
FIGS. 3A–3B is a comparison of MTT assay of Mosmann with the acid phosphatase assay using the cell count determination.
Figure 3B:
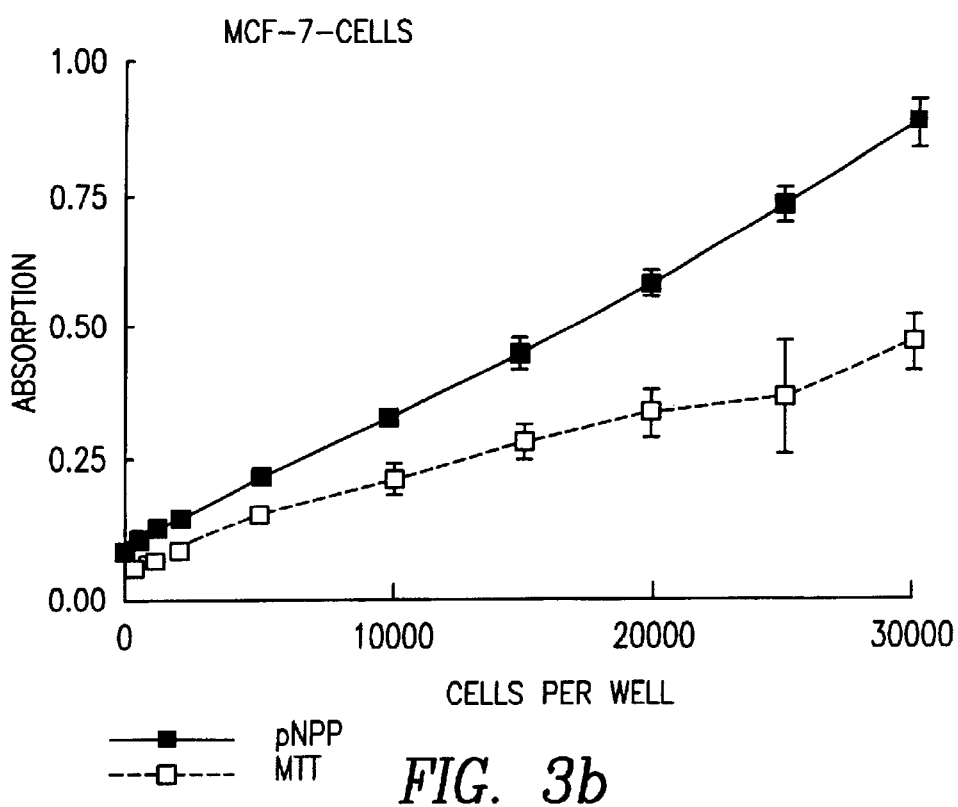
Figure 4A:
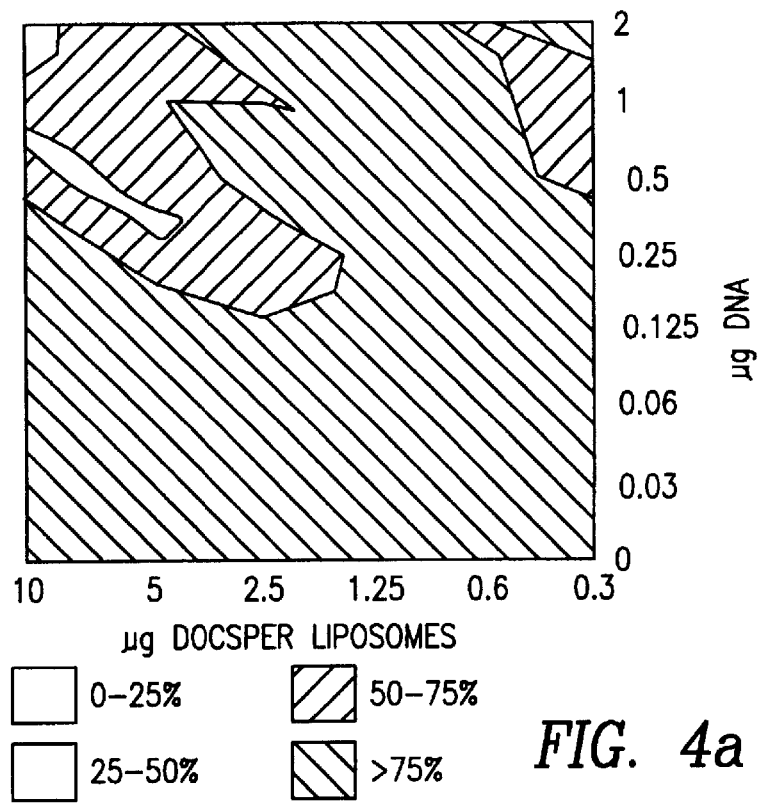
FIGS. 4A–4B is a comparison of MMT assay of Mosmann (A) and the β-galactosidase assay of Lim and chase (B) with de dual assay (C+D).
Figure 4B:
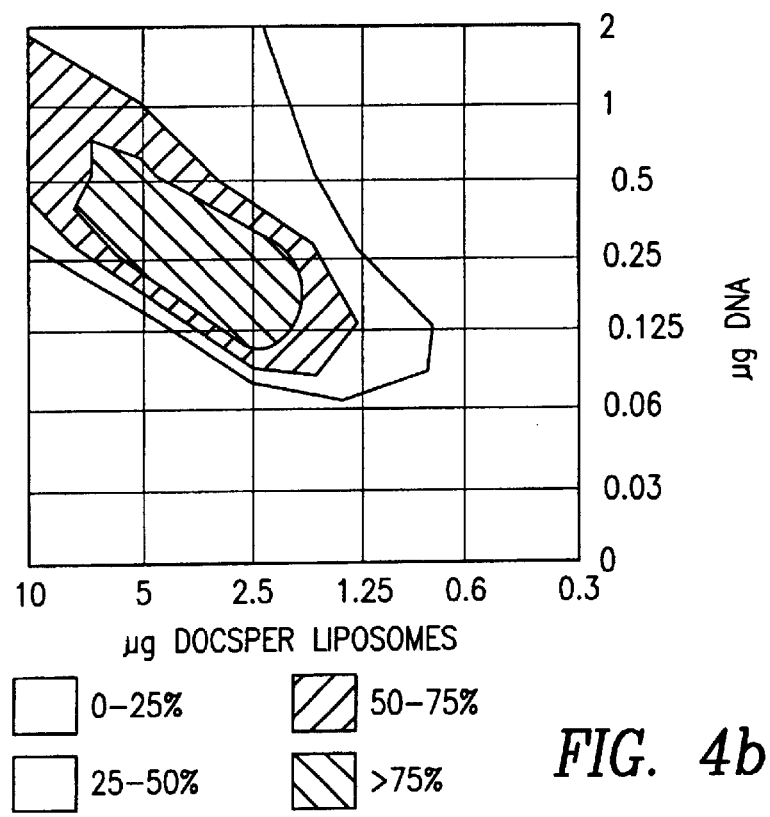
Figure 4C:
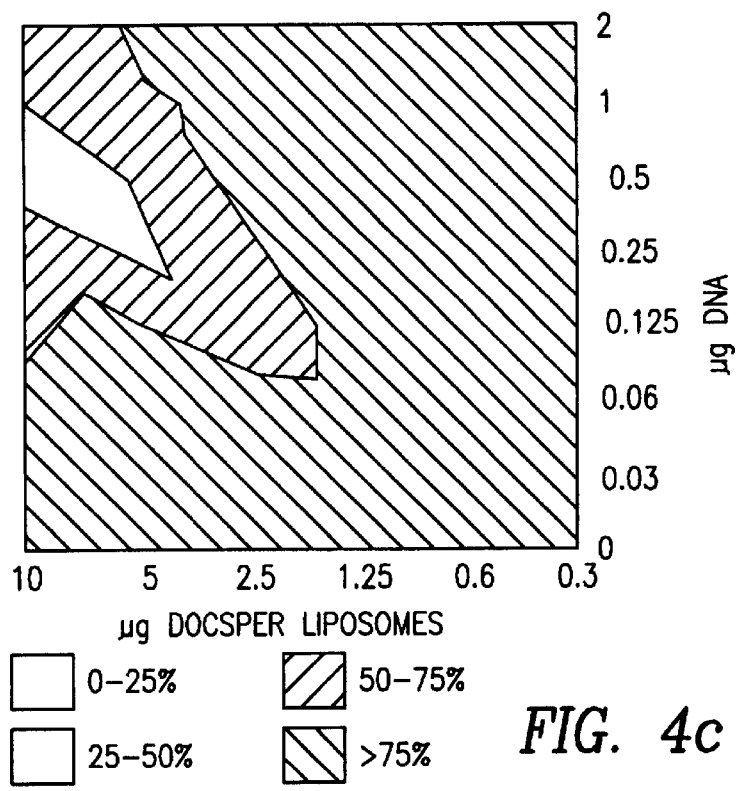
Figure 4D:
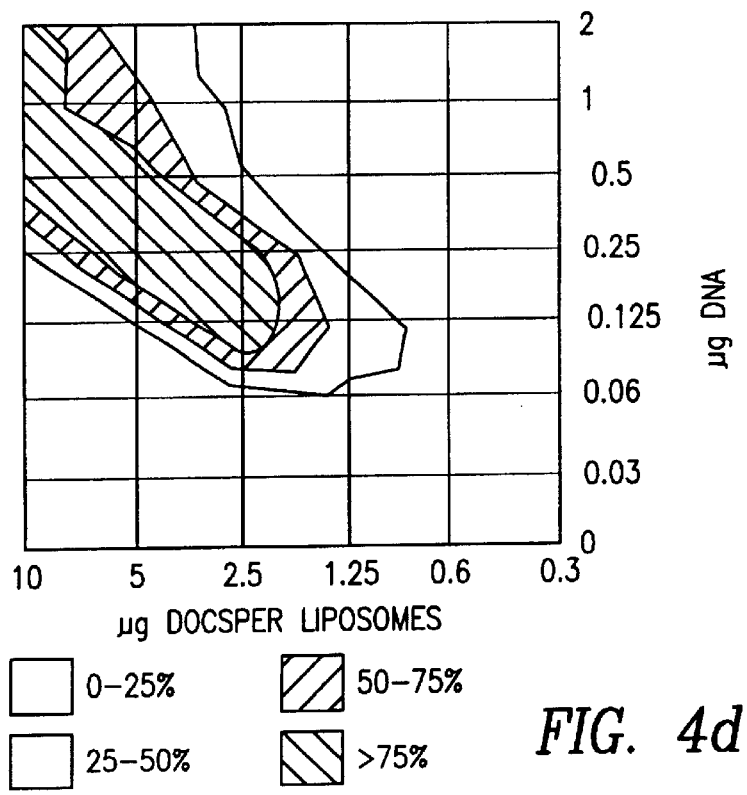

As shown in FIG. 3, after the cells are washed with PBS for the acid phosphatase test, the substrate buffer of 80 ml of 10 mM of pNPP in 0.02 M MES with 0.1% Triton X-100 (pH 5.5), 20 ml tris of Hcl (pH 8.0) for cell count determination is added (the exact volumes for the different plates investigated are given in Table 1). After incubating for 30 minutes at 37° C. and 5% carbon dioxide, the reaction is stopped by the addition of 0.5 M tris HCl or 0.5 M HEPES (having a pH of 8.0). Subsequently, the p-nitrophenol concentration is determined by determining the absorption at 405 nm (reference wavelength: 690 nm), using the microplate measuring device.

FIG. 4 compares the MTT assay of Mosmann (A), and the β-galactosidase assay of Lim and Chae (B), with the dual assay of the present invention (C+D). C represents the results of the acid phosphatase assay; and D represents the β-galactosidase assay after acid phosphatase assay. MCF-7 cells were transfected with DOCSPER liposomes and the plasmid DNA pUT 651 (Cayla, Toulouse, France) as described by Felgner et al. (1994). Three days after the transfection, the cell vitality and β-galactosidase expression were determined as in Example 1 (80 ml of 10 mM pNPP in 0.02 M MES; 0.1% Triton X-100 (pH 5.5), 20 ml of tris HCl (pH 8.0), 150 ml of 1 mg/ml CPRG in HBSS). The cell vitality of control cells and the maximum β-galactosidase expression of the experiment were set at 100%.

TABLE 1

Overview of the Volumes of the Different Test Buffers on Different Cell Culture Plates

|  | Acid Phosphatase Buffer (ml) | Stop Buffer (ml) | β-Galactosidase Test Buffer *(ml) |
|---|---|---|---|
| 96-Well Dish | 80 | 20 | 150 |
| 24-Well Dish | 240 | 60 | 450 |
| 6-Well Dish | 800 | 200 | 1,500 |

*It is also possible to use only 50 ml of β-galactosidase buffer for determining the β-galactosidase activity.

In the following examples the following buffers were employed:

| | |
|---|---|
| Acid phosphatase buffer: | 10 mM of pNPP in 0.02M of MES/0.1% of Triton X-100 |
| | 10 mM pNPP in 0.02M of sodium acetate/0.1% Triton X-100 |
| | 1 mM of naphthyl phosphate in 0.02 M sodium acetate/0.1% Triton X-100 |
| Stop buffer | 0.5M tris HCl (pH 8.0) |
| | 0.5M HEPES (pH 8.0) |
| β-galactosidase test buffer | 1 mg/ml CPRG in HBSS (50 ml) |
| | 2 mg/ml ONPG in HBSS (100 ml) |
| | 1 mM MUG in HBSS (100 ml); from MUG stock solution, 20 mM in DMSO and HBSS |

Transfection of the Cells

For the gene transfer investigations, 96-well flat-bottom cell culture plates are used. From 10,000 to 20,000 cells in 100 ml of medium with 10% fetal calf serum were sown per well. On the following day, the lipid/DNA complexes are prepared as follows (using the method of Feigner et al., 1994): In a separate plate, the lipid is diluted twice in serum-free medium commencing at 10 ml of lipid per well up to 0.31 mg of lipid per well at a total volume of 50 ml. Subsequently, the DNA is diluted also twice separately on a different 96-well plate, from 2 to 0.03 mg in 50 ml of also serum-free medium and, after that, the DNA dilution is pipetted onto the cells. For the complex formation, the mixture of the two dilutions is incubated for about 15 to 30 minutes at room temperature. The complexes are then added to the cells. After incubating for 3 to 5 hours, 100 ml of medium with 20% fetal calf serum are added and the cells are incubated for 24 to 72 hours for expressing the gene applied.

Dual Test of Toxicity and Reporter Gene Expression

From 24 to 72 hours after transfection of a lacZ reporter gene construct, cell vitality and toxicity of the method are determined by means of the acid phosphatase test. For this purpose, the cell culture medium is removed from the cells and the cells are washed once with 100 ml of PBS. The cell vitality and the gene expression are determined in different ways:

EXAMPLE 1

The cells are washed and 80 ml of the acid phosphatase test buffer is added (10 mM of pNPP in 0.02 M MES or 0.02 M sodium acetate /0.1% Triton X-100 for the cell lysis, pH of 5.5). After 30 minutes, the acid phosphatase reaction is stopped by the addition of 20 ml of 0.5 M tris HCl (or 0.5 M HEPES having a pH of 8.0). The cell count is calculated by the p-nitrophenol absorption at 405 to 450 nm. After the measurement of the p-nitrophenol concentration, the CPRG β-galactosidase test buffer (for example, 50 or 150 mg/ml of CPRG in HBSS) is added. Subsequently, the expression of the lacZ reported gene is analyzed with the help of the measurement of the optical absorption at 540 to 580 nm of the chlorophenol red reaction product 2 minutes to 24 hours after the addition of the β-galactosidase test buffer, depending on the level of the gene expression. The total height of the expression can be related to the values of the β-galactosidase calibration curve, which is treated in the same way as the cells.

EXAMPLE 2

The cells are washed, and 80 mL acid phosphatase buffer are added (10 mM pNPP in 0.02 M MES or 0.02 M sodium acetate/0.1% Triton X-100 for the cell lysis, pH 5.5). After 30 minutes, the acid phosphatase reaction is stopped by addition of 20 ml of 0.5 M tris HCl (or of 0.5 M HEPES, pH 8.0) The cell count is calculated by means of the p-nitrophenol absorption at 405 to 450 nm. After the p-nitrophenol concentration has been measured, the ONPG β-galactosidase test buffer is added (for example, 100 ml of 1 mg/ml ONPG in HBSS). Subsequently, the expression of the lacZ reporter gene is analyzed, 2 minutes to 24 hours after the addition of the ONPG β-galactosidase test buffer, depending on the level of gene expression, with the help of the measurement of of the optical absorption at 470 to 490 nm of the o-nitrophenol reaction product. The total height of the expression can be related to values of a β-galactosidase calibration curve, which is treated in the same way as the cells.

EXAMPLE 3

After the cells are washed, 80 μof the acid phosphatase test buffer are added (10 mM pNPP in 0.02 M MES or 0.02 M of sodium acetate/0.1% Triton X-100 for the cell lysis, pH 5.5). After 30 minutes, the acid phosphatase reaction is stopped by the addition of 20 μl of 0.5 M tris HCl (or of 0.5 M HEPES, pH 8.0). The cell count is calculated by means of the p-nitrophenol absorption at 405 to 450 nm. After the p-nitrophenol concentration has been measured, the MUG β-galactosidase test buffer is added (for example, 100 μl of 1 mM MUG in HBSS, 5% DMSO; from MUG stock solution, 20 mM in DMSO and HBSS). Subsequently, the expression of the lacZ reporter gene is analyzed, 2 minutes to 24 hours after the addition of the MUG β-galactosidase test buffer, depending on the level of the gene expression, with the help of the measurement of the light emission of the methyl umbelliferone reaction product at 460 to 540 nm after stimulation at about 350 nm. The total height of the expression can be related to values of a β-galactosidase calibration curve, which is treated in the same way as the cells.

EXAMPLE 4

After the cells are washed, 80 μl of the acid phosphatase test buffer are added (1 mM of naphthyl phosphate in 0.02 M sodium acetate buffer/0.1% Triton X-100 for the cell lysis, pH 5.5). After 2 to 4 hours, the acid phosphatase reaction is stopped by the addition of 20 μl of 0.5 M tris HCl (or 0.5 M of HEPES, pH 8.0). The cell count is calculated by the measurement of the light emission of the naphthol reaction product at about 405 nm after stimulation at about 350 nm. After measurement of the naphthol concentration, the MUG β-galactosidase test buffer is added (for example, 100 μl of 1 mM MUG in HBSS, 5% DMSO; from MUG stock solution, 20 mM in DMSO and HBSS). Subsequently, the expression of the lacZ reporter gene is analyzed, 2 minutes to 24 hours after the addition of the MUG β-galactosidase test buffer, depending on the level of gene expression, with the help of the measurement of the light emission of the methyl umbelliferone reaction product at 460 to 540 nm after stimulation at about 350 nm. The total height of the expression can be related to values of a β-galactosidase calibration curve, which is treated in the same way as the cells.

EXAMPLE 5

After the cells are washed, 80 μl of the acid phosphatase test buffer is added (10 mM pNPP in 0.02 M of sodium acetate buffer/0.1% Triton X-100 for the cell lysis, pH 5.5). After 30 minutes, the acid phosphatase reaction is stopped by the addition of 20 μof 0.5 M tris HCl (or 0.5 M HEPES, pH 8.0). The cell count is calculated by the p-nitrophenol absorption at 405 to 450 nm. After the p-nitrophenol concentration is measured, the ONPG MUG β-galactosidase test buffer is added (for example, 100 μl of 1 mM MUG, 7 mM ONPG, 5% DMSO; from MUG stock solution, 20 mM in DMSO and HBSS). Subsequently, the expression of the lacZ reporter gene is analyzed, 2 minutes to 24 hours after the addition of the ONPG MUG β-galactosidase test buffer, depending on the level of gene expression.

Gene expression is determined 1) with the help of the measurement of the light emission of the methyl umbelifferone reaction product at 460 to 540 nm after stimulation at about 350 nm, and 2) with the help of the measurement of the optical absorption at 470 to 490 nm of the o-nitrophenol reaction product.

The combination of two substrates enables very high β-galactosidase concentrations to be measured with the help of the ONPG substrate as well as very low ⊖-galactosidase concentrations to be determined with the help of the MUG substrate. By these means, the linearity of the test is extended over a larger range. The total height of the expression can be related to values of a β-galactosidase calibration curve, which is treated in the same way as the cells.

TABLE 2

Comparison of Different Methods for the Dual Determination
of Cell Vitality or Toxicity of the Gene Transfer Method
and of the Efficiency of the Gene Transfer Method

| Example | 1 | 2 | 3 | 4 | 5 |
|---|---|---|---|---|---|
| Acid phosphatase substrate | pNPP | pNPP | pNPP | naphthyl phosphate | pNPP |
| Acid phosphatase determination | optical | optical | optical | fluori-metric | optical |
| β-galactosidase substrate | CPRG | ONPG | MUG | MUG | MUG/ONPG |
| β-galactosidase determination | optical | optical | fluori-metric | fluori-metric | optical/ fluorimetric |
| β-galactosidase sensitivity | ++ | + | +++ | +++ | +++ |

We claim:

1. A process for determining cell vitality and efficiency after gene transfer in eukaryotic cells, by measuring reported acne activity which comprises determining in a reaction vessel the cell count of the transfected cells by a representative enzyme activity, and ascertaining in the same reaction vessel the efficiency of the gene transfer by determining the reporter gene activity after changing the pH.

2. The process of claim 1, wherein said determining by enzyme activity is carried out by determining the acid phosphatase activity.

3. The process of claim 1, which comprises reducing buffer strength for said ascertaining, of the efficiency of the gene transfer.

4. A dual test method for determination of cell vitality and efficiency after gene transfer in eukaryotic cells, which comprises the assay steps of (a) a vitality assay with a substrate for determining acid phosphatase activity, and a buffer for cell lysis, and (b) a reporter gene assay with a substrate for the reporter assay, and a buffer for determining the efficiency of the gene transfer.

5. The dual test method of claim 4, wherein said substrate in (a) is p-nitrophenyl phosphate (pNPP), and in (b) said substrate is used in a colorimetric β-galactosidase assay.

6. The dual test method of claim 4, wherein said substrate in (a) is pNPP, or naphthyl phosphate, and in (b) said substrate is used in a fluorimetric β-galactosidase assay.

* * * * *

UNITED STATES PATENT AND TRADEMARK OFFICE
CERTIFICATE OF CORRECTION

PATENT NO. : 6,692,913 B1
DATED : February 17, 2004
INVENTOR(S) : Detlev Groth and Regina Reszka It is certified that error appears in the above-identified patent and that said Letters Patent is hereby corrected as shown below:

Title page,
Item [75], Inventors, "Detlev Groth, Perch (DE)" should read -- Detlev Groth, Ferch (DE) --; and
Item [73], Assignee, "Max-Delbruck-Centrum fur Mdekular Medizin" should read -- Max-Delbrück-Centrum für Molekulare Medizin --

Signed and Sealed this

Fourth Day of May, 2004

JON W. DUDAS
*Acting Director of the United States Patent and Trademark Office*